(12) United States Patent
Gore et al.

(10) Patent No.: US 8,772,245 B2
(45) Date of Patent: Jul. 8, 2014

(54) CRYSTALLINE FORM OF CYCLOSPORINE A, METHODS OF PREPARATION, AND METHODS FOR USE THEREOF

(75) Inventors: Anuradha V. Gore, Irvine, CA (US); Kiomars Karami, Aliso Viejo, CA (US); Ke Wu, Irvine, CA (US); Richard S. Graham, Irvine, CA (US); Scott W. Smith, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/480,710

(22) Filed: May 25, 2012

(65) Prior Publication Data

US 2013/0023482 A1 Jan. 24, 2013

Related U.S. Application Data

(60) Provisional application No. 61/490,887, filed on May 27, 2011.

(51) Int. Cl.
*A61K 38/13* (2006.01)
*C07K 7/64* (2006.01)
*A61P 27/02* (2006.01)
*C07K 1/30* (2006.01)

(52) U.S. Cl.
CPC .............. *A61K 38/13* (2013.01); *C07K 7/645* (2013.01); *C07K 1/306* (2013.01); *A61K 9/048* (2013.01)
USPC ........................... 514/20.5; 530/321; 530/317

(58) Field of Classification Search
CPC ..... A61K 38/13; A61K 9/0048; C07K 7/645; C07K 1/306
See application file for complete search history.

(56) References Cited

U.S. PATENT DOCUMENTS

| 5,474,979 A | 12/1995 | Ding et al. |
| 6,254,860 B1 | 7/2001 | Garst |
| 6,350,442 B2 | 2/2002 | Garst |

FOREIGN PATENT DOCUMENTS

| GB | 2211848 A | 7/1989 | |
| WO | WO 2009/088570 A1 * | 7/2009 | ............. A61K 38/00 |

OTHER PUBLICATIONS

Cedarstaff, Thomas et al, 1983, A Comparative Study of Tear Evaporation Rates and Water Content of Soft Contact Lenses, American Journal of Optometry & Physiological Optics, 60(3), 167-174.
Lechuga-Ballesteros, David et al, Sep. 2003, Properties and Stability of a Liquid Crystal Form of Cyclosporine—Te First Reported Naturally occurring Peptide That Exists as a Thermotropic Liquid Crystal, Journal of Pharmaceutical Sciences, 92(9), 1821-1831.
Patent Cooperation Treaty, Notification of Transmittal of the International Search Report and the Written Opinion of the International Searching Authority, or the Declaration, Form PCT/ISA/220, Int. App. No. PCT/US2012/039611, May 25, 2012.

* cited by examiner

*Primary Examiner* — Julie Ha
*Assistant Examiner* — Li Ni Komatsu
(74) *Attorney, Agent, or Firm* — Laura L. Wine; Joel B. German; Debra D. Condino

(57) ABSTRACT

The present invention relates generally to crystalline forms of cyclosporine A and particularly to a newly identified form of cyclosporine A. The invention further relates to methods for its preparation and to methods for treating certain ocular disorders.

6 Claims, 7 Drawing Sheets

CRYSTALLINE FORM OF CYCLOSPORINE A, METHODS OF PREPARATION, AND METHODS FOR USE THEREOF

RELATED APPLICATIONS

This application claims priority to U.S. Provisional Patent Application No. 61/490,887 filed on May 27, 2011, the entire disclosure of which is incorporated herein by this reference.

FIELD OF THE INVENTION

The present invention relates generally to a new crystalline form of cyclosporine A and particularly pharmaceutical use of the newly identified form of cyclosporine A. The invention further relates to methods for its preparation and to methods for treating certain ocular disorders.

BACKGROUND OF THE INVENTION

The exposed part of a normal eye is covered by a thin tear film. The presence of a continuous tear film is important for the well-being of the corneal and conjunctival epithelium and provides the cornea with an optically high quality surface. In addition, the aqueous part of the tear film acts as a lubricant to the eyelids during blinking of the lids. Furthermore, certain enzymes contained in the tear fluid, for example immunoglobin A, lysozyme and beta lysin, are known to have bacteriostatic properties.

A sound lacrimal system functions to form and maintain a properly structured, continuous tear film. The lacrimal apparatus consists of the secretory system (the source), the distribution system, and the excretory system (the sink). In the secretory system, aqueous tears are supplied by main and accessory lacrimal glands.

The bulk of the tear film is made of such aqueous tear. The continuous production and drainage of aqueous tear is important in maintaining the corneal and conjunctival epithelium in a moist state, in providing nutrients for epithelial respiration, in supplying bacteriostatic agents and in cleaning the ocular surface by the flushing action of tear movement.

Surgical procedures have been suggested in the management of dry eye states. Where there has been significant conjunctival destruction, mucous membrane transplants have been advocated. It has also been suggested that parotid (saliva) duct transplantation can be useful in the management of dry eyes. However, surgical alterations to combat dry eye conditions constitute a dramatic remedy and any benefit resulting from these alterations is questionable.

Other diseases of the eye include phacoanaphylactic endophthalmitis, uveitis, and keratoconjunctivitis sicca (KCS). These diseases can be located throughout the eye, in both the posterior and anterior chambers of the eye as well as in the vitreous body.

Uveitis, the inflammation of the uvea, is responsible for about 10% of the visual impairment in the United States. Phacoanaphylactic endophthalmitis is a human autoimmune disease.

Panuveitis refers to inflammation of the entire uveal (vascular) layer of the eye. Posterior uveitis generally refers to chorioentinitis, and anterior uveitis refers to iridocyclitis. The inflammatory products (i.e. cells, fibrins, excess proteins) of these inflammations are commonly found in the fluid spaces if the eye, i.e. anterior chamber, posterior chamber and vitreous space as well as infiltrating the tissue intimately involved in the inflammatory response. Uveitis may occur following surgical or traumatic injury to the eye; as a component of an autoimmune disorder, i.e. rheumatoid arthritis, Behcet's disease, ankylosing spondylitis, sarcoidosis; as an isolated immune mediated ocular disorder, i.e. pars planitis, iridocyclitis etc., unassociated with known etiologies; and following certain systemic diseases which cause antibody-antigen complexes to be deposited in the uveal tissues. Together these disorders represent the non-infectious uveitities.

Phacoanaphylaxis is a severe form of uveitis in which the lens in the causative antigen. The lens proteins are normally secluded by the lens capsule since before birth. When these proteins are released into the eye by injury or by surgery or occasionally during cataract development, they can become intensely antigenic and incite an autoimmune response. If the response is moderate it is seen as chronic uveitis. If it is very fast in progression the eye becomes seriously inflamed in all segments. This latter response is named phacoanaphylaxis.

Cyclosporines are a group of nonpolar cyclic oligopeptides with known immunosuppressant activity. Cyclosporin A, along with several other minor metabolites, as well as cyclosporin B, C, D, E, F, G, H, I, J, K, L, M, N, O, P, Q, R, S, T, U, V, W, X, Y and Z, have been identified. The use of cyclosporine A and cyclosporine A derivatives to treat the ophthalmic conditions set forth above has been the subject of various patents, for example Ding et al U.S. Pat. No. 5,474,979; Garst U.S. Pat. No. 6,254,860; and Garst U.S. Pat. No. 6,350,442, the disclosure of each of which is incorporated in its entirely herein by reference. With respect to its solid state chemistry, cyclosporine A (CsA) is known to exist in an amorphous form, liquid crystal form, tetragonal crystalline form (Form 1), and an orthorhombic form (Form 3).

SUMMARY OF THE INVENTION

The present invention provides a new crystalline form of CsA, with unique and novel properties suitable for pharmaceutical development.

In another embodiment of the invention, there are provided pharmaceutical compositions including a therapeutically effective amount of cyclosporine A in a new crystalline form in an ophthalmically acceptable carrier.

In another embodiment there are provided methods for treating an aqueous deficient dry eye state, uveitis or phacoanaphylactic endophthalmitis in an eye. Such methods can be performed, for example, by administering to a subject in need thereof cyclosporine A in crystalline form 2 in an ophthalmically acceptable carrier.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

In addition, it is to be understood that "crystalline form" and "pseudomorphic form" may be used interchangeably throughout the specification. "Crytalline form 1" or "crystalline form 2" may also be referred to as "Pseudomorph 1" or "Pseudomorph 2".

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

Figure 1:
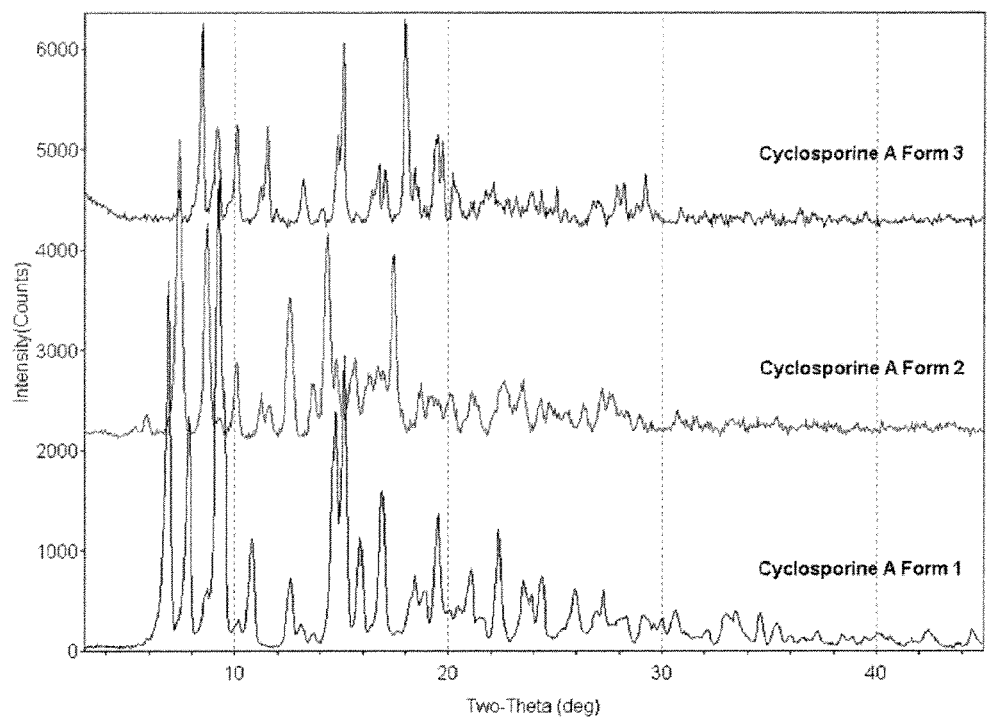
FIG. 1 depicts characteristic X-ray powder diffraction (XRPD) patterns of CsA in a new crystalline form (designated as Form 2 herein), tetragonal form (designated as Form 1 herein), and orthorhombic form (designated as Form 3 herein).

The present invention provides a new crystalline form of CsA, designated cyclosporine A Form 2. The XRPD pattern of this novel Form 2 differs significantly from the tetragonal form and orthorhombic form (FIG. 1). The major crystalline peaks for CsA form 2 appear at (2θ) when scanned by an X-ray diffractometer with X-ray source as Cu Kα radiation, λ=1.54 Å, at 30 kV/0.15 mA: 7.5, 8.8, 10.2, 11.3, 12.7, 13.8, 14.5, 15.6 and 17.5 (d-spacing in crystal lattice at about 11.8, 10.0, 8.7, 7.8, 7.0, 6.4, 6.1, 5.6 and 5.1 Å, respectively, FIG. 2). These major peaks are defined as those being unique to Form 2 relative to the orthorhombic or tetragonal forms; as well as, peaks having an intensity greater than 5 times the background.

In one embodiment, the new crystalline form (Form 2) of CsA is a nonstoichiometric hydrate of Cyclosporin A.

In another embodiment, the crystalline Form 2 is represented by the formula:

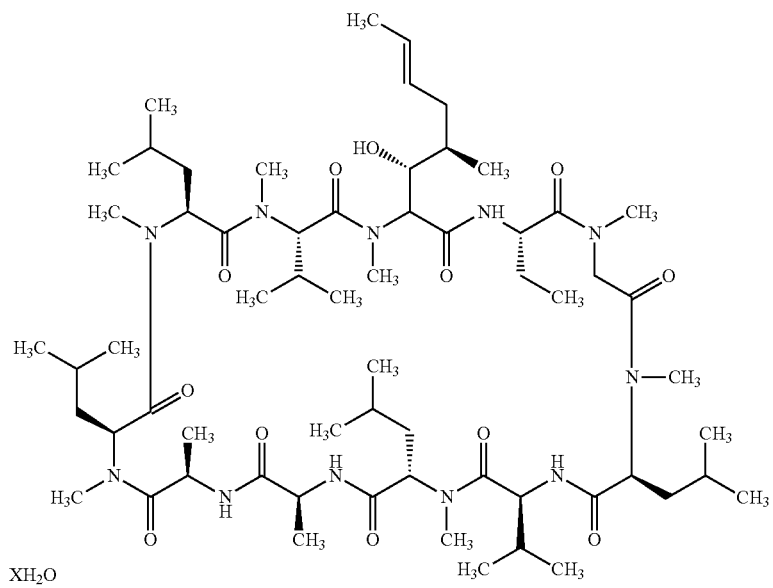

wherein X is the number of molecules of water and varies from 0-3. In one embodiment, X in the above formula is 2.

Form 2 appears to be a kinetically stable form of CsA in aqueous suspensions. Suspensions containing Form 2 show no conversion to other known polymorphic or pseudomorphic forms upon storage. It has been found that Form 1 and the amorphous form convert to Form 2 in the presence of water. The single crystal structure of the newly discovered hydrate form of cyclosporine A (Form 2) was determined and the crystal structure parameters are listed in Table 2. These results indicate that Form 2 is a unique compared to other known crystalline forms of cyclosporine A.

TABLE 1

Crystal data and data collection parameters of crystal structure solution of CsA Form 2.

| | |
|---|---|
| formula | $C_{52}H_{115}N_{11}O_{14}$ |
| formula weight | 1238.67 |
| space group | $P\,2_1\,2_1\,2_1$ (No. 19) |
| a (Å) | 12.6390(5) |
| b (Å) | 19.7582(8) |
| c (Å) | 29.568(2) |
| volume (Å$^3$) | 7383.8(7) |
| Z | 4 |
| $d_{calc}$ (g cm$^{-3}$) | 1.114 |
| crystal dimensions (mm) | 0.27 × 0.18 × 0.12 |
| temperature (K) | 150 |
| radiation (wavelength in Å) | Cu K$_3$ (1.54184) |
| monochromator | confocal optics |
| linear abs coef (mm$^{-1}$) | 0.640 |
| absorption correction applied | empirical[3] |
| transmission factors (min, max) | 0.60, 0.93 |
| diffractometer | Rigaku RAPID-II |
| h, k, l range | −13 to 13 −21 to 21 −32 to 21 |
| 2θ range (deg) | 5.38-115.00 |
| mosaicity (deg) | 1.31 |
| programs used | SHELXTL |
| $F_{coo}$ | 2704.0 |

TABLE 1-continued

Crystal data and data collection parameters
of crystal structure solution of CsA Form 2.

| | |
|---|---|
| weighting | $1/[\sigma 2(F_o^2) + (0.0845P)^2 + 0.0000P]$ where $P = (F_o^2 + 2F_c^2)/3$ |
| data collected | 37360 |
| unique data | 9964 |
| $R_{int}$ | 0.077 |
| data used in refinement | 9964 |
| cutoff used in R-factor calculations | $F_o^2 > 2.0\ s(F_o^2)$ |
| data with $I > 2.0\ s(I)$ | 6597 |
| number of variables | 834 |
| largest shift/esd in final cycle | 0.00 |
| $R(F_c)$ | 0.061 |
| $R_w(F_o^2)$ | 0.145 |
| goodness of fit | 1.037 |
| absolute structure determination | Flack parameter[b] (0.0(3)) |

Figure 7:
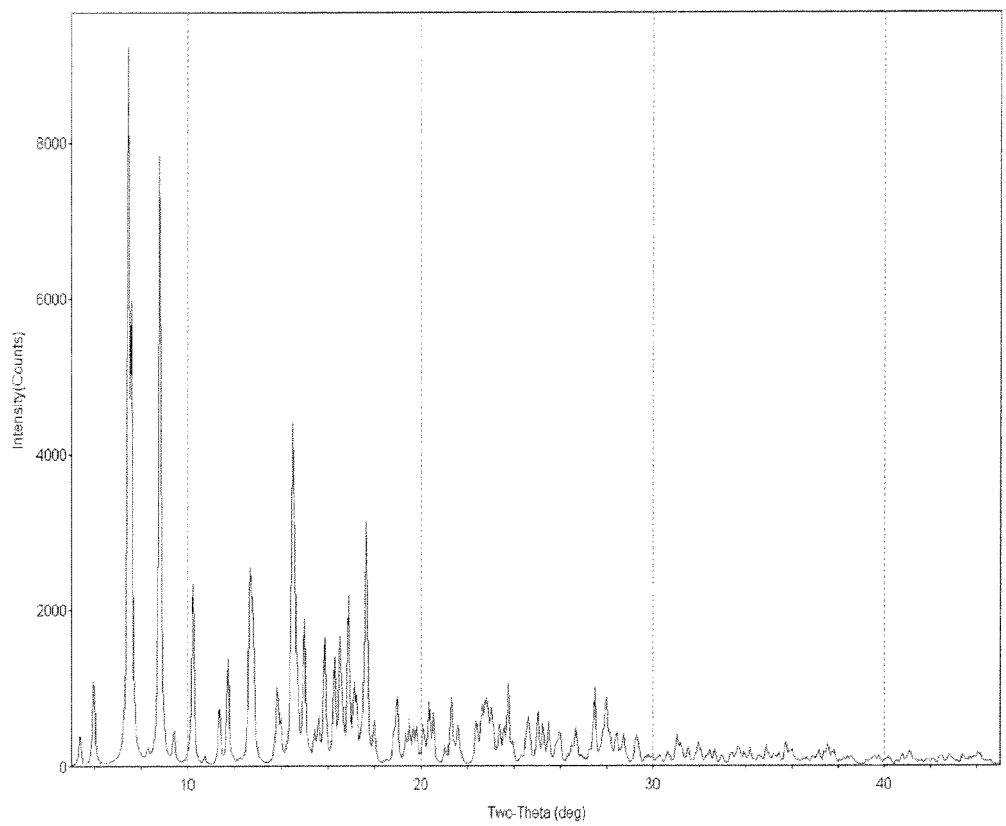
FIG. 7 depicts the simulated XRPD pattern of cyclosporine A forms.

The asymmetric unit of this CsA Form 2 was found to contain one cyclosporine A molecule and two water molecules. It is possible that any small molecule that can hydrogen bond to water could play the role of space filler, which would give a range of potential structures running from the orthorhombic dihydrate to distorted monoclinic dihydrate. The XRPD pattern calculated from the single-crystal structure is shown in FIG. 7 and it matches the experimental pattern shown in FIG. 2. These matching patterns further corroborate that Form 2 is a unique and pure crystalline form of cyclosporine A.

Figure 3:
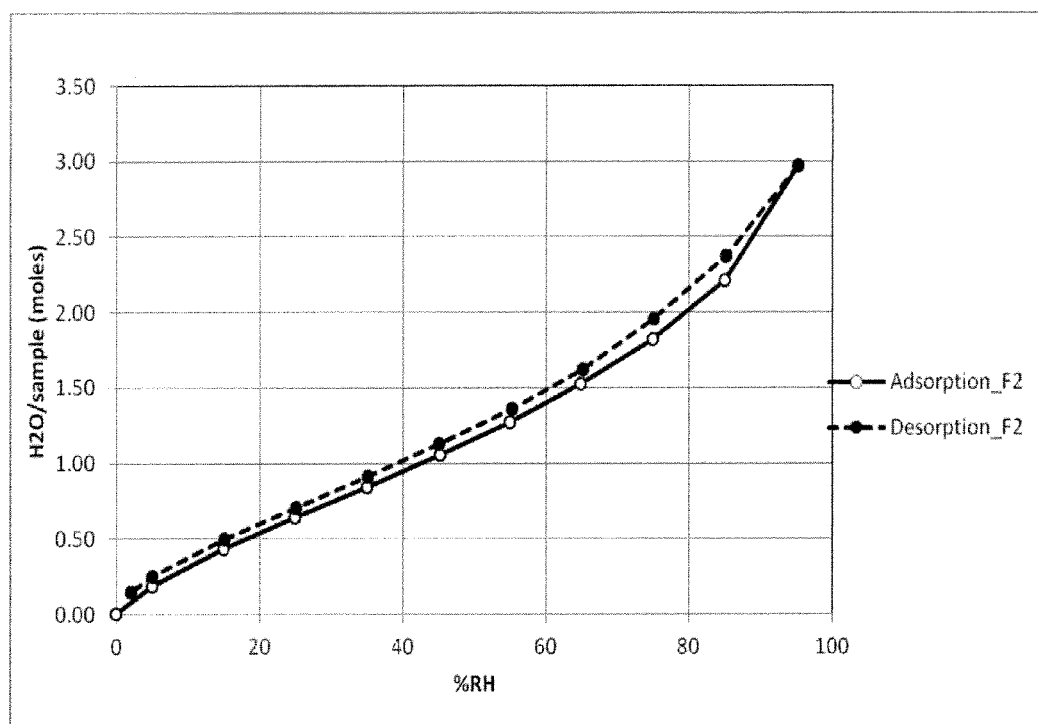
FIG. 3 depicts the water sorption/desorption profile of CsA Form 2.
Figure 4:
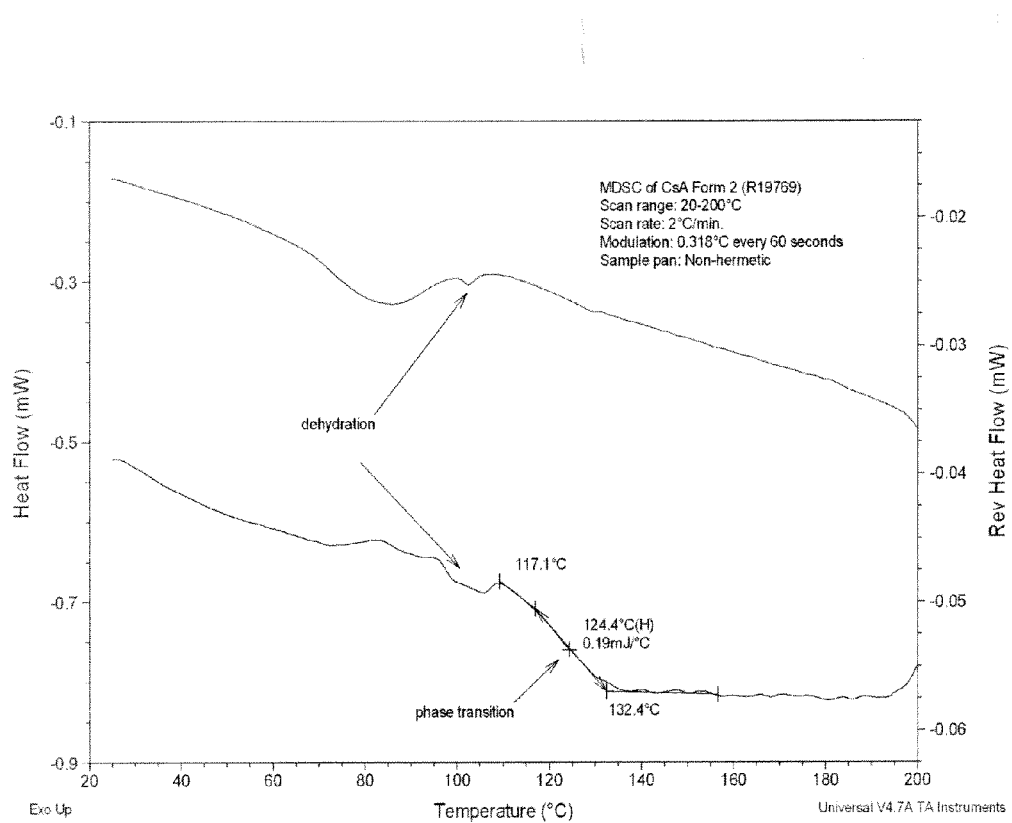
FIG. 4 depicts MDSC analysis of CsA Form 2 recovered from 0.04% formulation with 1% PS80.

Without wishing to be bound by theory, thermogravimetric analysis combined with KF titration and vapor sorption desorption analysis (VSA) suggest that CsA Form 2 is a non-stoichiometric hydrate of CsA. The vapor sorption analysis of Cyclosporine Form 2 indicates that water content in the new crystal form reversibly varies with relative humidity as shown in FIG. 3. Similar to the tetragonal form, the new CsA form undergoes a phase transition to a liquid crystal or amorphous form at 124.4° C. prior to melting as indicated by the modulated differential calorimetric (MDSC) analysis (FIG. 4).

The new physical form of CsA has a higher solubility (130 μg/mL) than orthorhombic form (100 μg/mL) in ophthalmic formulation vehicles containing 1% PS80. This is desirable for developing solution or suspension formulations. The new form appears to be a more stable form than the tetragonal in aqueous solution. Form 2 offers some advantages over the tetragonal and orthorhombic forms in alternative formulations
such as ocular implants, tablets, capsules and semi-solid formulations, liquid gel capsules, suspensions and micro-emulsions.

In addition, it has been discovered that Form 2 is more readily millable than Forms 1 or 3. Milling is very important since, in a Cyclosporin A sustained release suspension, large particles (i.e., ≥40 μm) have been observed to settle in a 2% hyaluronic acid (hydrogel) formulation and to be difficult to re-suspend. The CsA Form 2 is readily milled to 10 μm or smaller. Physically stable suspensions of these crystals have been prepared at concentrations of up to 10% in 2.5% hyaluronic acid.

In addition to physical stability, it is anticipated that smaller particle size will deliver more drug to the tissue, by virtue of the increased surface area. Reducing particle size for this reason may be critical because Form 2 appears to have lower dissolution characteristics than the amorphous form and therefore will likely have lower delivery to the tissue, although the smaller particle size may mitigate this problem. Indeed, it has been discovered that making nanoparticles is easier with Form 2 than Forms 1 or 3. So, if it is required to nanosize the crystals in order to improve drug delivery to the tissue and/or to improve the physical stability of the suspension, Form 2 provides a distinct advantage over other forms.

Pharmaceutical compositions may be prepared by combining a therapeutically effective amount of CsA Form 2 according to the invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

Ingredient Amount (% w/w) active ingredient about 0.001-5 preservative 0-0.10 vehicle 0-40 tonicity adjustor 0-10 buffer 0.01-10 pH adjustor q.s. pH 4.5-7.5 antioxidant as needed surfactant as needed purified water as needed to make 100%

The actual dose of the active compounds of the present invention depends on the specific compound, and on the condition to be treated; the selection of the appropriate dose is well within the knowledge of the skilled artisan.

The pharmaceutical compositions containing CsA Form 2 are useful in treating a variety of ocular disorders. Thus, in another embodiment of the invention there are provided methods for treating an aqueous deficient dry eye state, uveitis, phacoanaphylactic endophthalmitis, or keratoconjunctivitis sicca (KCS) in an eye, comprising administering to a subject in need thereof cyclosporine A in crystalline form 2 in an ophthalmically acceptable carrier.

One aspect of the present invention relates to pharmaceutical compositions for alleviating dry eye related symptoms, for example, as in patients having immune mediated keratoconjunctivitis sicca (KCS) or dry eye disease or other autoimmune dysfunction of the lacrimal gland, as well as dry eye symptoms of contact lens wearers.

Dry eye generally refers to any tear film abnormality, usually with epithelial abnormalities. A specific deficiency of the aqueous component of the tear film is known as keratoconjunctivitis sicca (KCS), which affects about 30 million people worldwide. It is usually included as part of Sjogren's syndrome. Literally the term denotes inflammation of the cornea and conjunctiva secondary to drying.

When the tear film fails to perform its functions of lubrication, oxygenation, and removal of debris, symptoms of foreign body sensation (grittiness, scratchiness, sandiness), fatigue, and dryness result. A patient may experience severe pain, especially in the presence of filamentary keratopathy. Loss of the smooth refractive surface of the tear film causes blurred vision, which can vary from blink to blink, accounting for a variable manifest refraction and for complaints of variable vision throughout the day. Surface drying may produce reflex tearing and the misleading complaint of excess tears. Typically, symptoms of tear deficiency are worse late in the day, with prolonged use of the eyes (as when the patient reads or watches television), and in conditions of heat, wind, and low humidity (as on the beach or ski slopes). Symptoms that are worse in the morning suggest an associated chronic blepharitis, recurrent corneal epithelial erosion, or exposure keratopathy. Further, symptoms include superficial punctate erosions, corneal filaments, coarse mucus plaques, and epithelial defects.

As hereinabove noted, most of these symptoms result from the unstable tear film and abnormal ocular surface that diminish the ability of the ocular surface to respond to environmental challenges. Dry eye syndrome, if left untreated, can cause progressive pathological changes in the conjunctival and corneal epithelium.

The etiologies of dry eye are varied. The disease generally referred to as "dry eye" may be the result of age-related decreases in systemic androgen support to the lacrimal gland or systemic autoimmune diseases such as Sjogrens Syndrome. A growing body of research suggests that dry eye is the result of an underlying cytokine and receptor-mediated inflammatory process.

Palliative agents, such as tear replacement, tear preservation, and autonomic tear stimulation, may provide complete or partial relief of symptoms. However, therapeutic treatments directed at the underlying inflammatory process may prove beneficial in correcting the underlying disorder.

The tear film in a normal eye consists of a thin (about 6-45 um in thickness) film composed of a mucous layer lying over the corneal epithelium and an aqueous layer covering the mucous layer and epithelium, which is in turn covered by an extremely thin (0.01-0.22 um) layer of lipid molecules.

The presence of a continuous tear film is important for the well-being of the corneal and conjunctival epithelium and provides the cornea with an optically high quality surface. In addition, the aqueous part of the tear film acts as a lubricant to the eyelids during blinking of the lids. Furthermore, certain enzymes contained in the tear fluid, for example, immunoglobulin A, lysozyme and beta lysin, are known to have bacteriostatic properties.

It is believed that the lipid layer is responsible for retarding evaporation of water from the eye. If the lipid layer of the tear film is disturbed by, for example, trauma, disease, irritation of the eye or contact lens wear, excessive evaporation of water from the eye may occur, leaving the surface of the eye "dry" (see e.g., Cedarstaff and Tomlinson, Am. J. Optometry & Physiol. Optics, 60:167-174, 1983 [tear film disruption in patients with keratoconjunctivitis sicca, or "dry eye"]).

A normal lacrimal system functions to form and maintain a properly structured, continuous tear film. The lacrimal system consists of the secretory system (the source), the distribution system and the excretory system (the sink). In the secretory system, aqueous tears are supplied by the main and accessory lacrimal glands.

Excessive evaporation of water from the tear film results in ocular discomfort (frequently experienced by the person as dryness or tired eyes or other less frequently reported discomfort symptoms) and may eventually lead to physiological and pathological changes in the tissue of the eye, especially in the cornea. For contact lens wearers, such discomfort is particularly acute because the loss of water from the tear film occurs at the interface between the tear film and the lens. Further, if the lens is a hydrogel "soft" lens, excessive evaporation of water from the tear film can also result in excessive evaporation of water from the lens.

Thus taking into account this evaporation, the continuous production and drainage of aqueous tear is important to maintaining the corneal and conjunctval epithelium in a moist state, in providing nutrients for epithelian respiration, in supplying bacteriostatic agents and in cleaning the ocular surface by the flushing action of tear movement.

In relatively mild cases, the main symptom of KCS is a foreign body sensation or a mild "scratchiness". This can progress to become a constant, intense burning irritative sensation which can be debilitating to the patient. More severe forms of KCS progress to the development of filamentary keratitis, a painful condition characterized by the appearance of numerous strands or filaments attached to the corneal surface. Recent evidence suggests that these filaments represent breaks in the continuity of the normal corneal epithelial cells. The shear created by lid motion pulls these filaments, causing pain. Management of this stage of KCS is very difficult.

A frequent complication of KCS is secondary infection. Several breakdowns in the eye's normal defense mechanism seem to occur, presumably attributable to a decrease in the concentration of antibacterial lysozyme in the aqueous tears of a patient suffering from KCS.

Normally, aqueous-deficient dry eye states, such as, for example, KCS, are treated by supplementation of the tears with artificial tear substitutes. However, relief is limited by the retention time of the administered artificial tear solution in the eye. Typically, the effect of an artificial tear solution administered to the eye dissipates within about thirty to forty-five minutes. The effect of such products, while soothing initially, does not last long enough. The patient is inconvenienced by the necessity of repeated administration of the artificial tear solution in the eye as needed to supplement the normal tears.

The following examples are intended only to illustrate the present invention and should in no way be construed as limiting the subject invention.

EXAMPLES

Example 1

A 0.05 wt % CsA aqueous solution containing 1% w/v Tween 80 was prepared and stored at 65° C. The new crystalline form of cyclosporine formed by precipitation after 24 hrs of storage.

Example 2

Cyclosporine A (30.19 g) was suspended in 900 mL of 1% w/v Tween 80 in water at room temp. The suspension was heated to 65° C. and seeded with 0.2 g of Cyclosporine A Form 2 at 52° C. The suspension was stirred for 22-23 hours at 65-61° C. Precipitated solid was recovered by vacuum filtration, washed with water, and dried under vacuum first at 40° C., then at room temp. The yield was 30.3 g

Example 3

Figure 5:
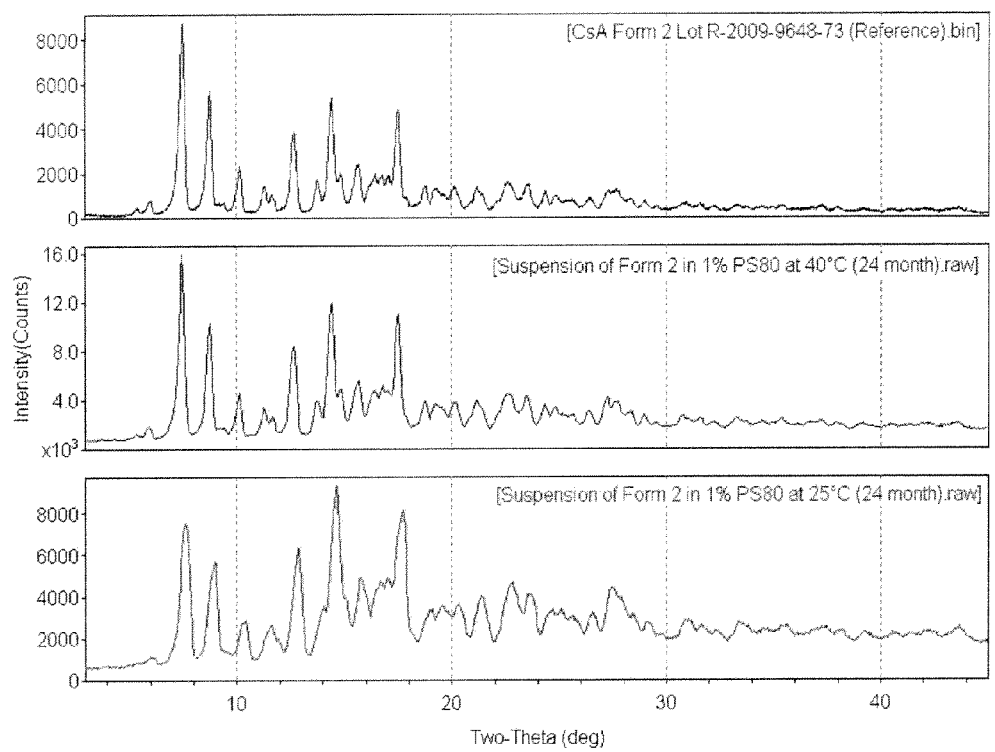
FIG. 5 depicts the XRPD diffractograms for samples collected from an aqueous suspension containing 1% w/v polysorbate 80 and excess CsA Form 2 after storage for 24 months.

Aqueous suspensions containing 1 w/v % polysorbate 80 (PS80) and excess CsA Form 2 were prepared and stored at 25° C. and 40° C. Samples of the solid residue were collected over a 24-month period and analyzed by X-ray powder diffraction. FIG. 5 shows the XRPD diffractograms for samples collected after 24 months. Compared to the reference diffractogram of Form 2, there are no changes indicating Form 2 is physically stable under the conditions tested.

Example 4

Figure 6:
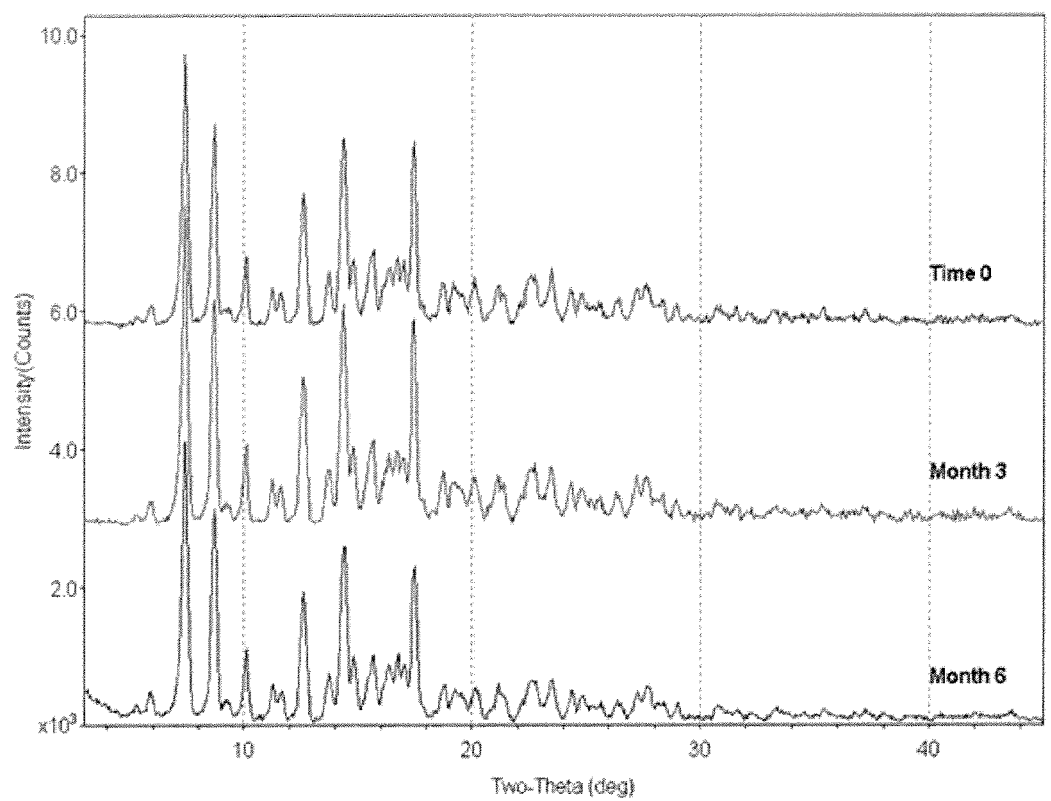
FIG. 6 depicts the XRPD diffractograms for samples collected from an aqueous suspension containing 5% w/v hyaluronic acid and excess CsA Form 2 after storage for 6 months.

A suspension of cyclosporine Form 2 in 5% w/v hyaluronic acid gel in water was prepared and stored at 25° C. Samples were collected over a 6 month time period and analyzed by X-ray powder diffraction. FIG. 6 shows the XRPD diffractograms for samples collected after 6 months. Compared to the reference diffractogram of Form 2, there are no changes indicating Form 2 is physically stable under the conditions tested.

While this invention has been described with respect to these specific examples, it is understood that other modifications and variations are possible without departing from the spirit of the invention.

What is claimed is:

1. Cyclosporine A having the structure

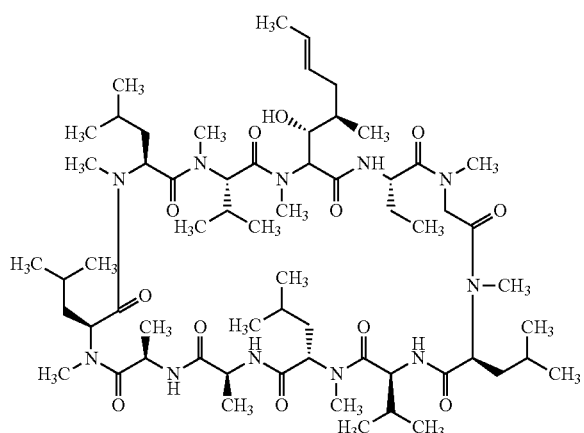

in crystalline form 2.

2. A crystalline form of cyclosporine A having an X-ray powder diffraction pattern with major peaks at (2θ): 7.5, 8.8, 10.2, 11.3, 12.7, 13.8, 14.5, 15.6 and 17.5.

Figure 2:
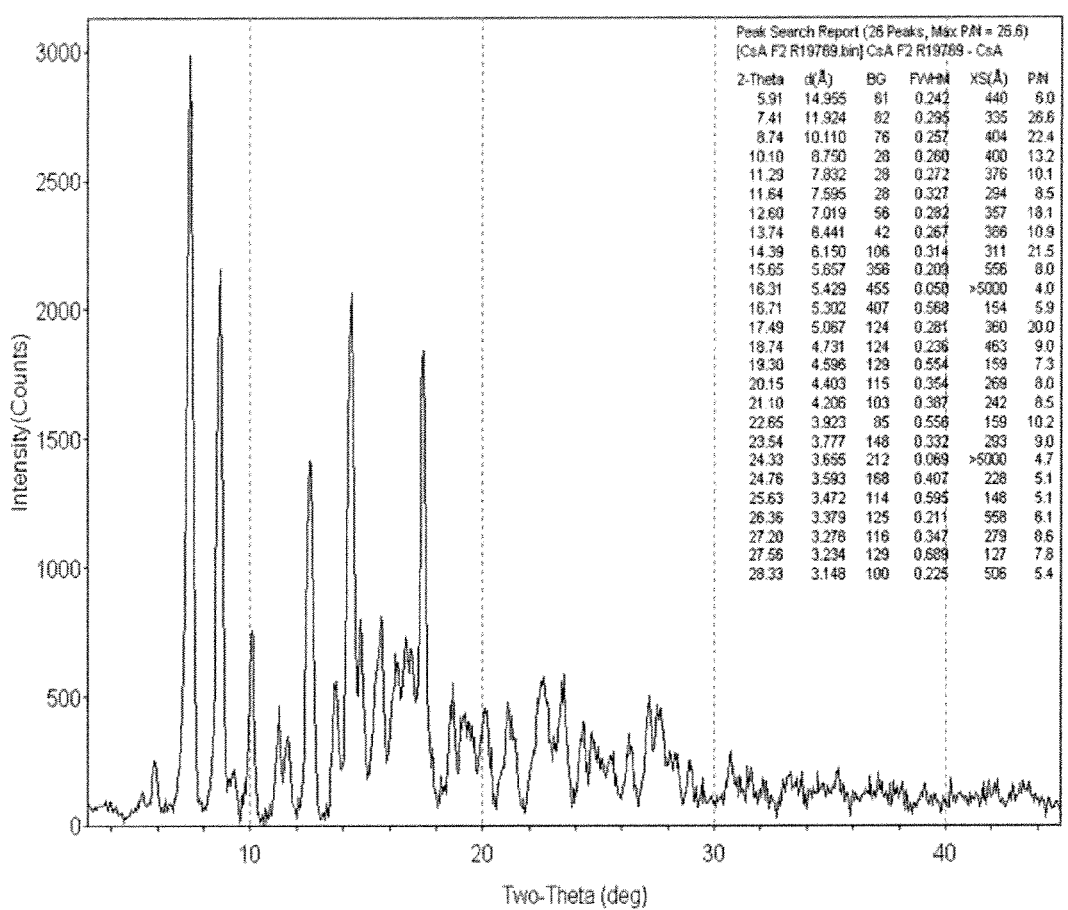
FIG. 2 depicts the XRPD diffractogram of CsA crystalline Form 2.

3. A crystalline form of cyclosporine A having the X-ray diffraction pattern as shown in FIG. 2.

4. The crystalline form of claim 1 free of other crystalline forms.

5. A crystalline form as set forth by the formula

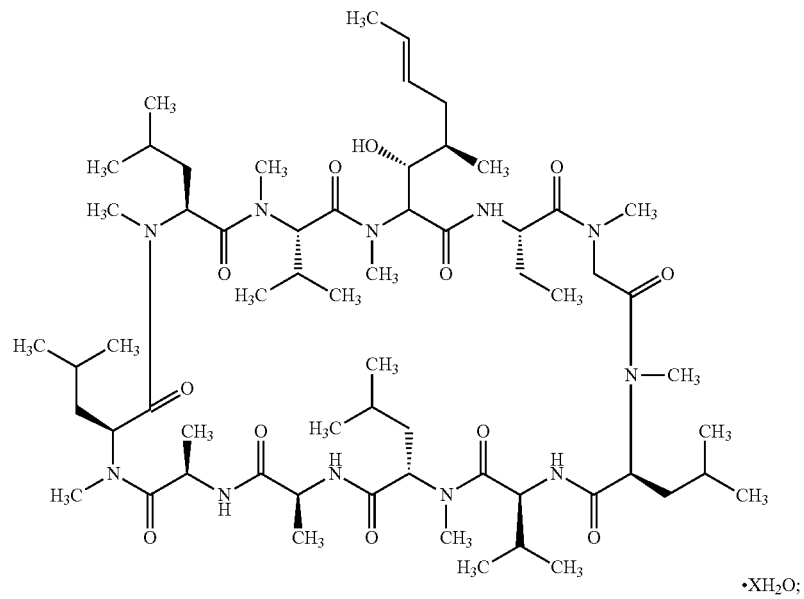 [SMILES: C/C=C/C[C@@H](C)[C@@H](O)C1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

·XH$_2$O;

wherein X is 0-3.

6. The crystalline form of claim 5, wherein X is 2.

* * * * *